US00PP37631P2

(12) United States Plant Patent
Mislow, III

(10) Patent No.: US PP37,631 P2
(45) Date of Patent: Aug. 18, 2026

(54) ***FICUS* PLANT NAMED 'GM3X25001'**

(50) Latin Name: *Ficus lyrata*
Varietal Denomination: GM3X25001

(71) Applicant: Gregory J. Mislow, III, Miami, FL (US)

(72) Inventor: Gregory J. Mislow, III, Miami, FL (US)

( * ) Notice: Subject to any disclaimer, the term of this patent is extended or adjusted under 35 U.S.C. 154(b) by 0 days.

(21) Appl. No.: 19/203,971

(22) Filed: May 9, 2025

(51) Int. Cl.
*A01H 5/12* (2018.01)
*A01H 6/00* (2018.01)

(52) U.S. Cl.
USPC ..... Plt./211

(58) Field of Classification Search
USPC ..... Plt./211
CPC ..... A01H 5/12; A01H 5/00; A01H 6/00
See application file for complete search history.

*Primary Examiner* — June Hwu
(74) *Attorney, Agent, or Firm* — The Webb Law Firm

(57) ABSTRACT

A new and distinct variety of *Ficus* plant having variegated light green leaves with a dark green center that grows more compactly in the shade.

8 Drawing Sheets

Botanical classification: *Ficus lyrata.*
Varietal Denomination: 'GM3X25001'.

BACKGROUND OF THE NEW PLANT

The present invention relates to a new and distinct cultivar of *Ficus*, botanically known as *Ficus lyrata.*

The new *Ficus* was discovered by the Inventor in August 2021, in a controlled environment in Miami, Florida. Specifically, the new *Ficus* was discovered in a greenhouse in a group of young plants. The parent plant is an unnamed species of *Ficus lyrata* and the plant was discovered as a whole plant mutation. Asexual propagation of the new cultivar by cuttings since February 2025, in Miami, Florida, has shown that the unique features of this new *Ficus* are stable and reproduced true to type in successive generations.

SUMMARY OF THE INVENTION

The following traits have been repeatedly observed and are determined to be unique characteristics of the new *Ficus*. These characteristics in combination distinguish the new *Ficus* as a new and distinct cultivar:

1. Variegated leaf
2. Light green leaf with dark green center
3. Grows more compact in shade Plants of the new *Ficus* can be compared to regular *Ficus lyrata*. In side-by-side comparisons conducted by the Inventor in Miami, FL, plants of the new *Ficus* differed from regular *Ficus lyrata* in the following characteristics:

1. Plants of the new *Ficus* have variegated leaves colored light green with a dark green center, while *Ficus lyrata* has solid green leaves.
2. More tolerant to low light

DESCRIPTION OF THE DRAWINGS

The accompanying colored photographs illustrate the overall appearance of the new *Ficus*, showing the colors as true as it is reasonably possible to obtain in colored reproductions of this type. Colors in the photographs may differ slightly from the color values cited in the detailed botanical description, which accurately describes the colors of the new *Ficus.*

The photograph of FIG. 1 comprises a side perspective view of the new *Ficus* grown under partial shade in a 17 inch pot.

Figure 1:
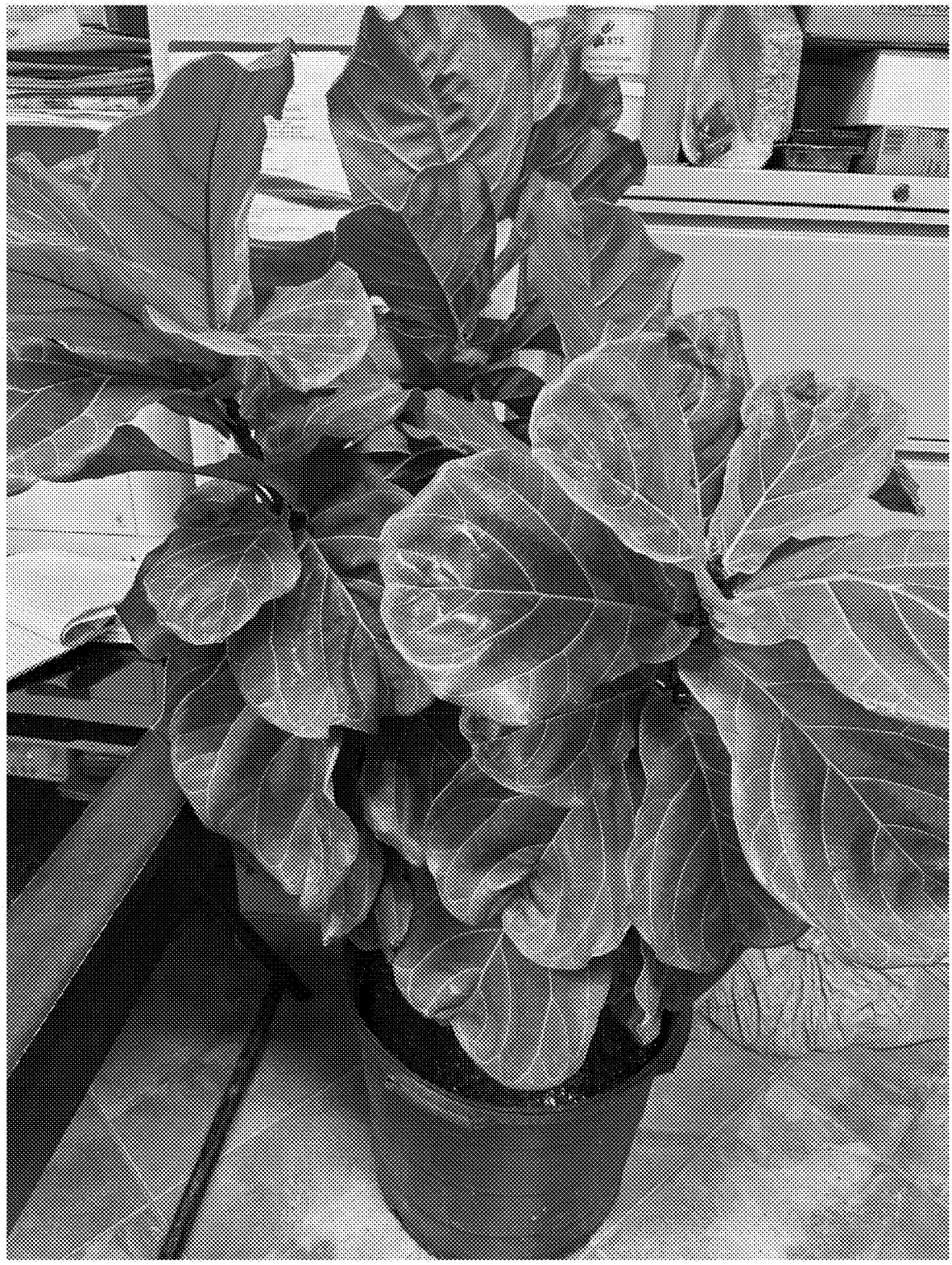
Figure 2:
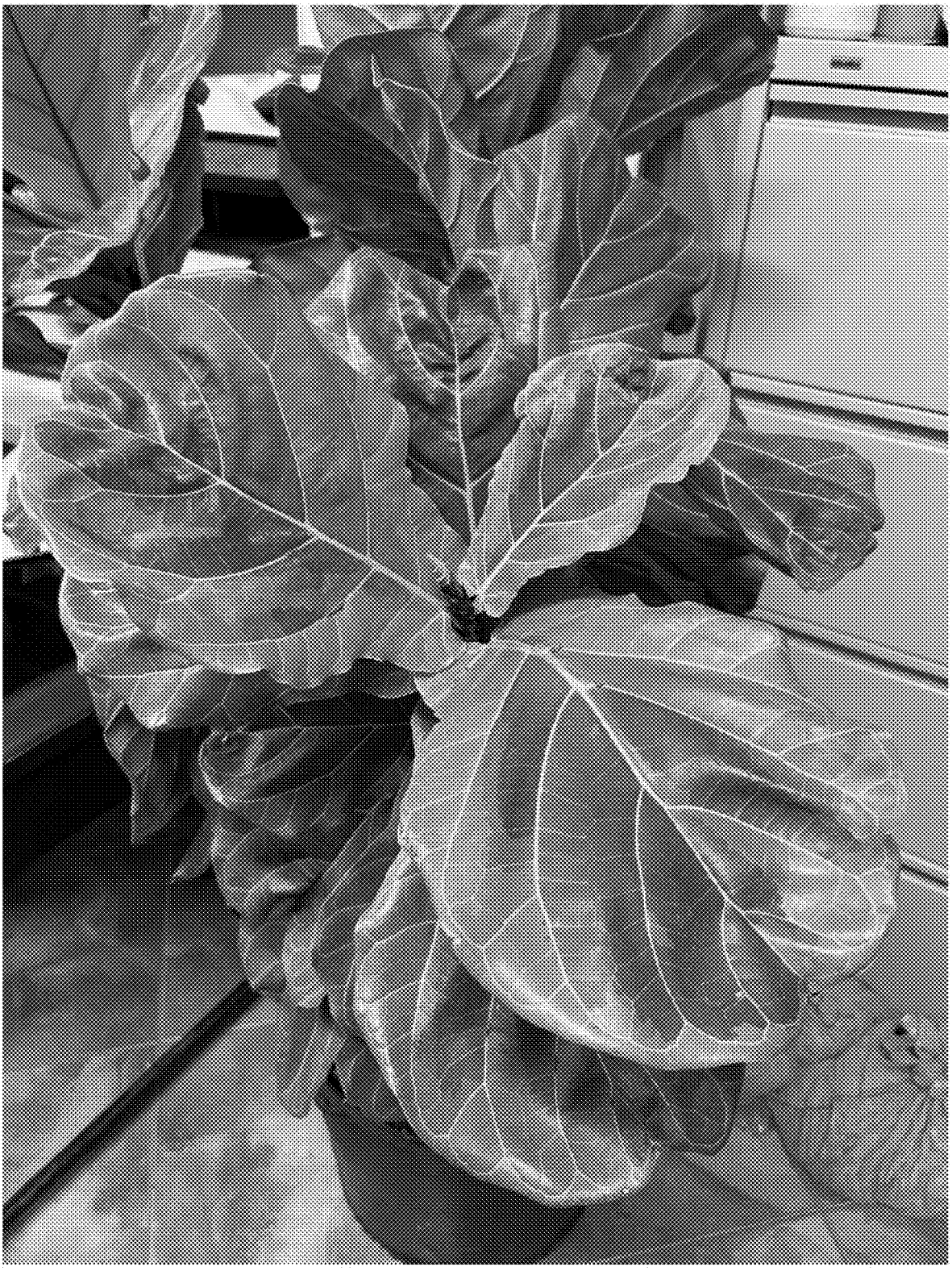

The photograph of FIG. 2 comprises a close-up view of typical leaves of the new *Ficus.*

Figure 3:
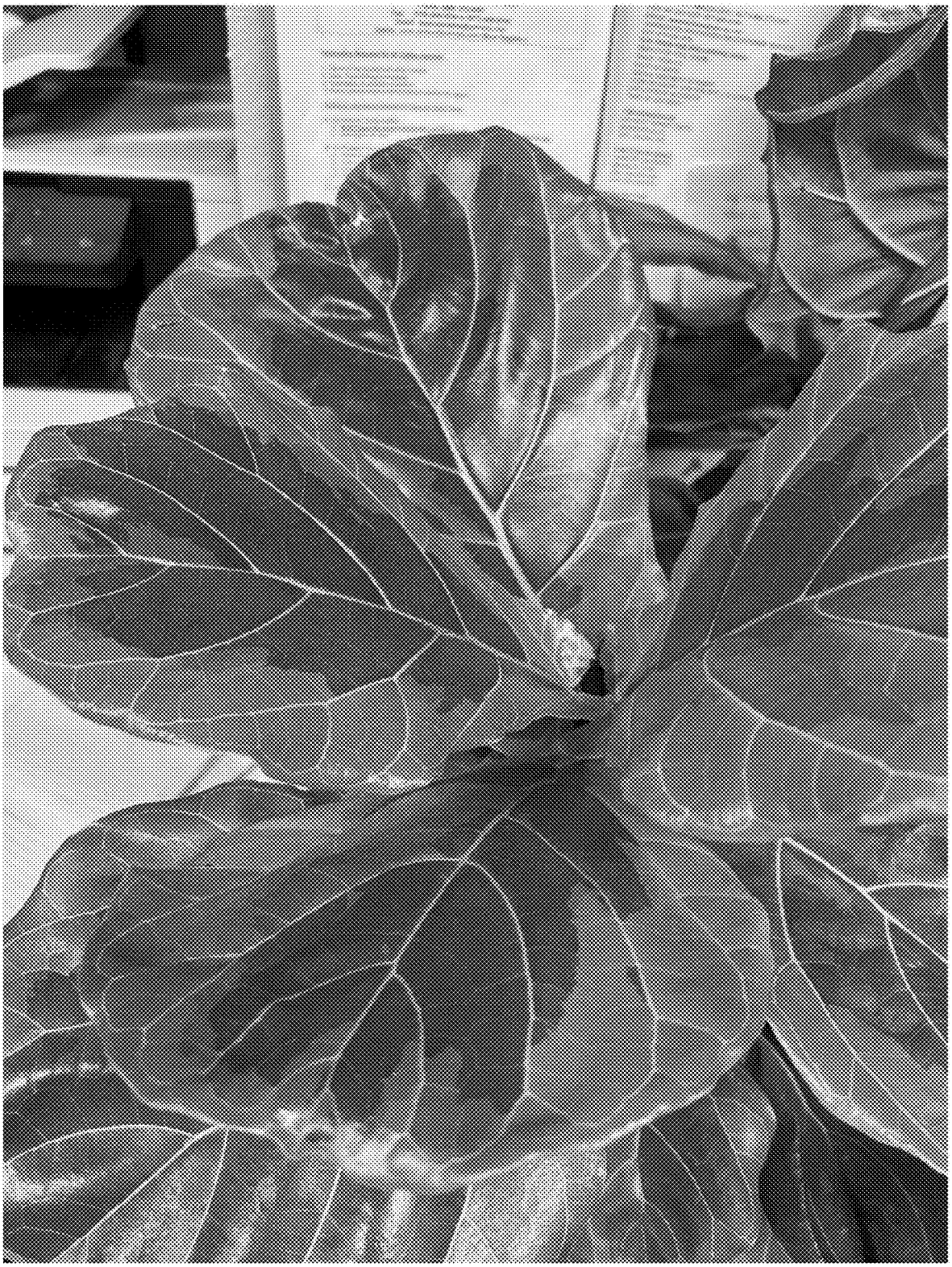

The photograph of FIG. 3 comprises a close-up view of typical leaves of the new *Ficus.*

Figure 4:
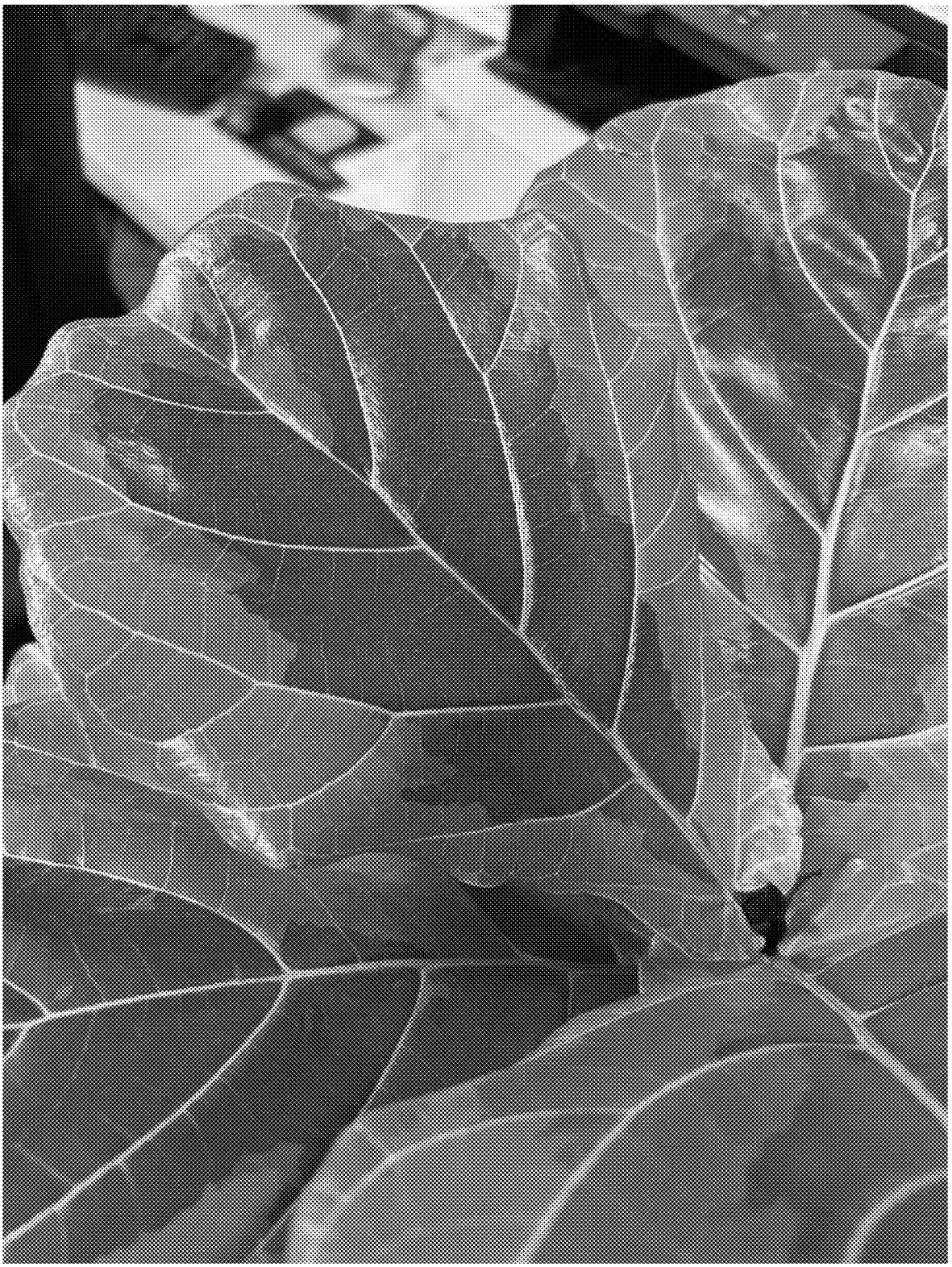

The photograph of FIG. 4 comprises a close-up view of typical leaves of the new *Ficus.*

Figure 5:
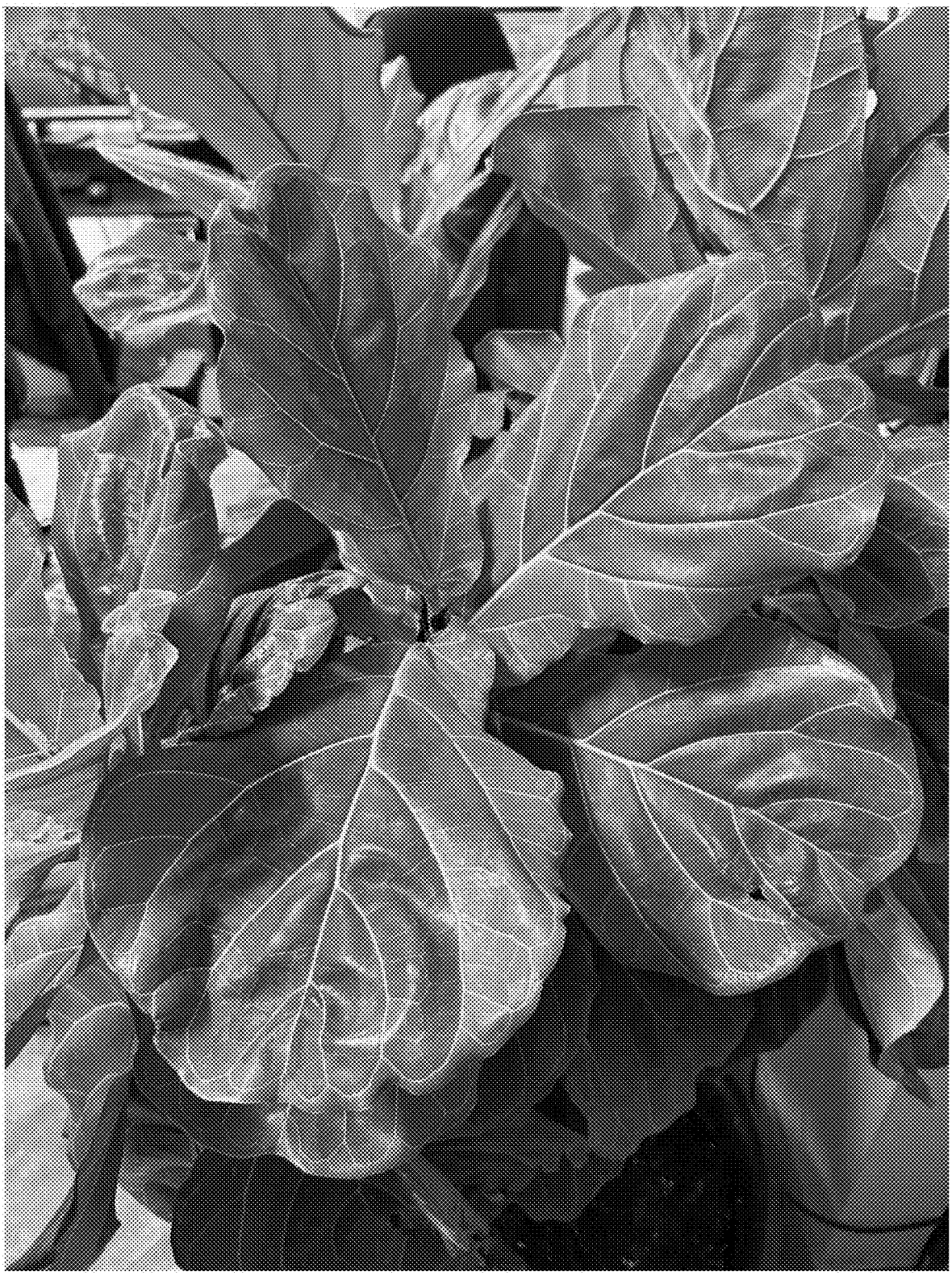

The photograph of FIG. 5 comprises a close-up view of typical leaves of the new *Ficus.*

Figure 6:
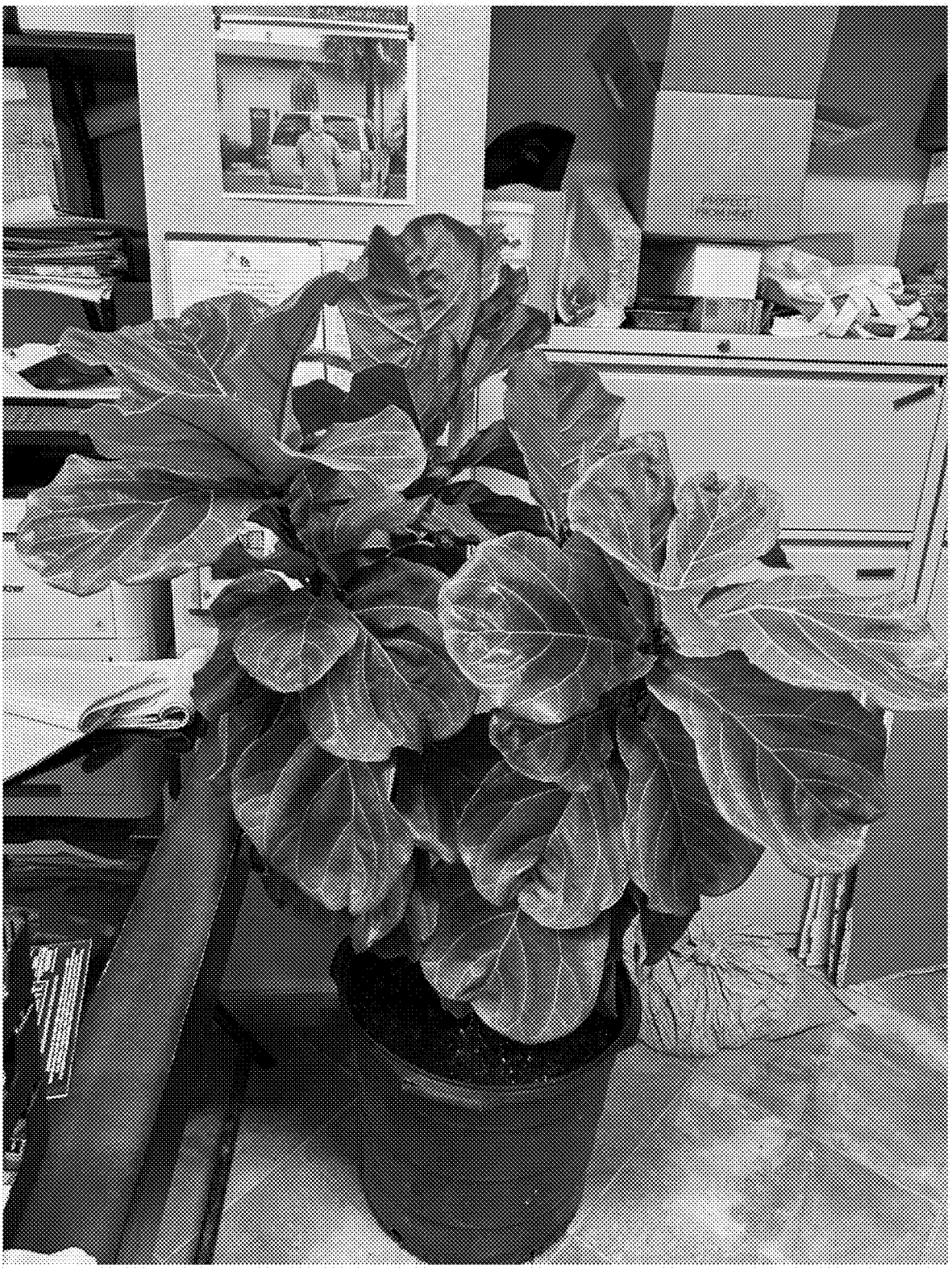

The photograph of FIG. 6 comprises a side perspective view of a typical plant of the new *Ficus.*

Figure 7:
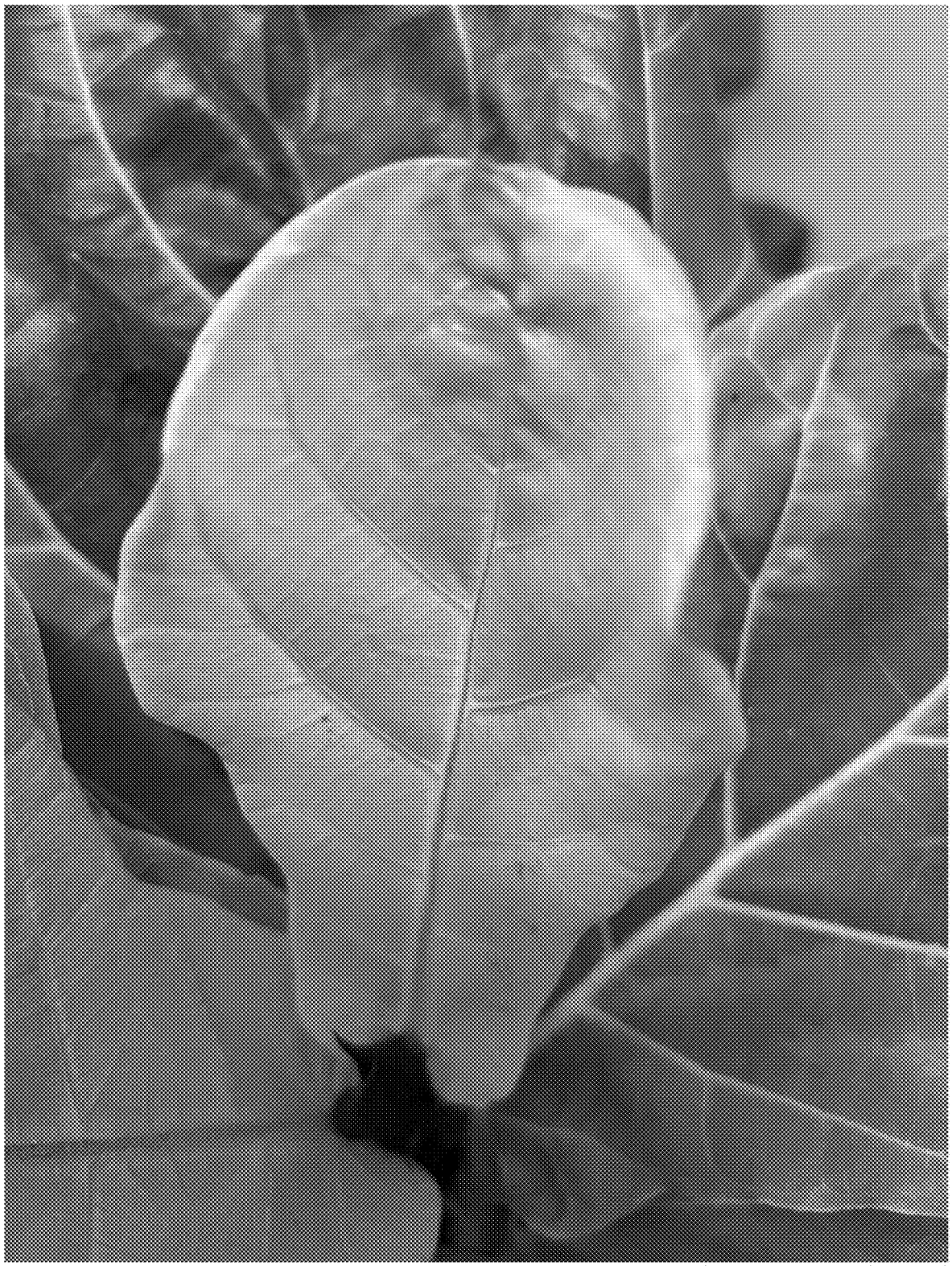

The photograph of FIG. 7 comprises a close-up view of typical new growth leaves of the new *Ficus.*

Figure 8:
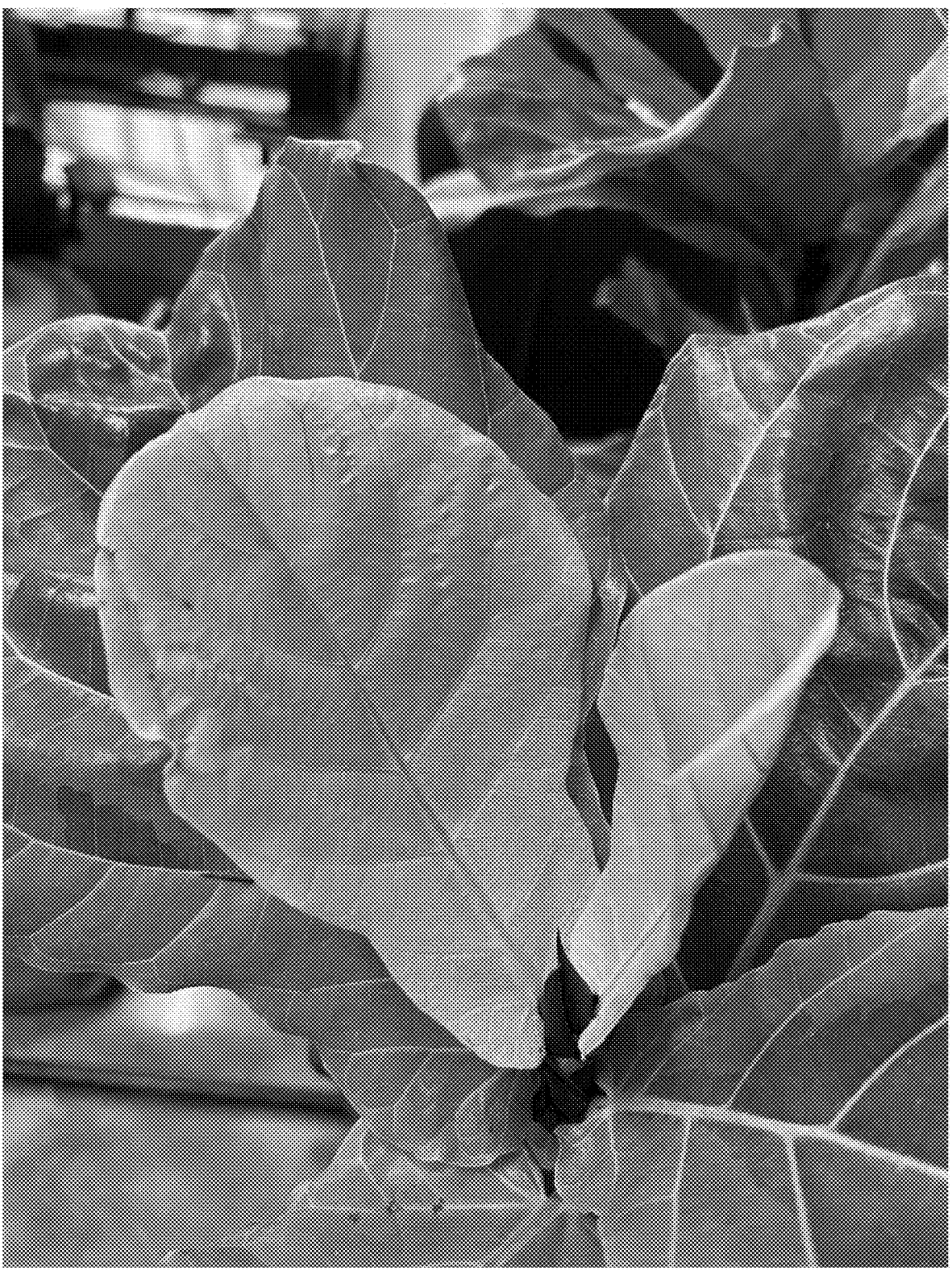

The photograph of FIG. 8 comprises a close-up view of typical new growth leaves of the new *Ficus.*

DESCRIPTION OF THE PLANT

The cultivar *Ficus* has not been observed under all possible environmental conditions. The phenotype may vary somewhat with variations in environment such as temperature and light intensity without, however, any variance in genotype.

The aforementioned photographs and following observations and measurements describe plants of the new *Ficus* that were grown in an outdoor nursery in Miami, Florida. During the production of the plants, day temperatures averaged about 82° F. and night temperatures averaged about 82° F. Plants used for the photographs were about 3 years from planting. Plants used for the description were about 3.5 years from planting. Color references are made to The Royal Horticultural Society Colour Chart, version 2001, except where general terms of ordinary dictionary significance are used.

PLANT

Botanical classification: *Ficus lyrata.*

Propagation:

*Type*.—By cuttings.

*Time to initiate roots*.—About 21 days at 82° F.

*Time to produce a rooted plant*.—About 45 days at 82° F.

*Root description*.—Branching, 1C, 2C, 6D, 22A.

Plant description:

*Appearance*.—Upright growth with branching when pruned. Mounded and symmetrical.

*Growth rate/vigor*.—Strong.

*Plant height*.—About 5 ft.

*Branching habit*.—Minimal branching habit.

*Main stems*.—Number: Four. Length: About 38 inches. Diameter: About 1 inch. Internode length: About 1 inch. Attitude: Straight Growth Habit. Aspect: Vertical. Strength: Strong. Texture: Rough. Bark: Flakey. Color: Grey-brown N199B at dry flakey bark & Grey-brown N199C at the younger bark. Size: Approximately 0.5 inch by 1 inch.

*Foliage*.—Length: About 12 inches. Width: About 7-8 inches. Shape: Fiddle shape. Shape of Apex: Round. Shape of Base: Obtuse. Orientation and aspect: Spiral. Texture: Smooth; no pubescence. Glossiness: High gloss. Margin shape: Undulate. Intensity of undulation: Moderate. Young leaves: Upper surface color: 139A, 137A, 143C, 143B. Lower surface color: 145A. Fully expanded leaves: Upper surface color: 143A, 139A. Lower surface color: 145A. Venation: Upper surface color: 153A, 153B, 153C, 153D; ranging from darker at the tip of leaf to lighter by the base of stem. Lower surface color: 145A, 144C, 166A. Petiole: Length: About 1 inch. Diameter: About ¼ inch. Strength: Medium. Texture: Glossy, coarse. Color: 143C. Stipule: Shape: Awl-shaped. Shape of Apex: Broad apex. Shape of Base: Narrowly triangular-lanceolate. Length: About 1½-2 inch. Diameter: About ¼-½ inch. Texture: Upper Surface: Coarse. Lower Surface: Coarse. Color of both upper and lower surfaces: 166A.

Flower: Flower development has not been observed on plants of the new *Ficus* grown under commercial production conditions.

Disease/pest resistance:

*Disease resistance*.—Additional disease resistance has not been observed on plants of the new *Ficus* grown under commercial production conditions.

*Pest resistance*.—Additional pest resistance has not been observed on plants of the new *Ficus*.grown under commercial production conditions.

Weather tolerance:

*Temperature tolerance*.—About 46° F.-96° F.

*Drought tolerance*.—Good.

What is claimed is:

1. A new and distinct variety of *Ficus lyrata* plant, named 'GM3X25001' substantially as illustrated and described herein.

* * * * *